United States Patent [19]
Simon, Jr.

[11] Patent Number: 5,479,022
[45] Date of Patent: Dec. 26, 1995

[54] ELECTRON CAPTURE DETECTOR WITH GUARD ELECTRODE

[75] Inventor: Richard K. Simon, Jr., College Station, Tex.

[73] Assignee: Varian Associates, Inc.

[21] Appl. No.: 261,573

[22] Filed: Jun. 17, 1994

[51] Int. Cl.6 .................................................. G01T 1/18
[52] U.S. Cl. ............................................ 250/382; 250/375
[58] Field of Search ................................. 250/382, 374, 250/375

[56] References Cited

U.S. PATENT DOCUMENTS 3,629,574  12/1971  Carroll ................................. 250/282

OTHER PUBLICATIONS

Bruschi et al, "A Method for Det. Electron Mobility and Attachment to Molecular Impurities in High Density Gases", J. Phys. E. Sci. Instrument vol. 18, (1985) p. 239.

Primary Examiner—Davis L. Willis
Assistant Examiner—Richard Hanig
Attorney, Agent, or Firm—Gerald M. Fisher

[57] ABSTRACT

An improved ECD employing an ECD cell having a third electrode, i.e. guard positioned between the ECD cell field electrodes. The guard electrode is physically interposed between said field electrodes to divert all leakage current in the support insulators which flow between the field electrodes. The guard electrode ECD cell provides improved linear dynamic range as well as avoiding deterioration from handling during manufacture or repair.

16 Claims, 8 Drawing Sheets

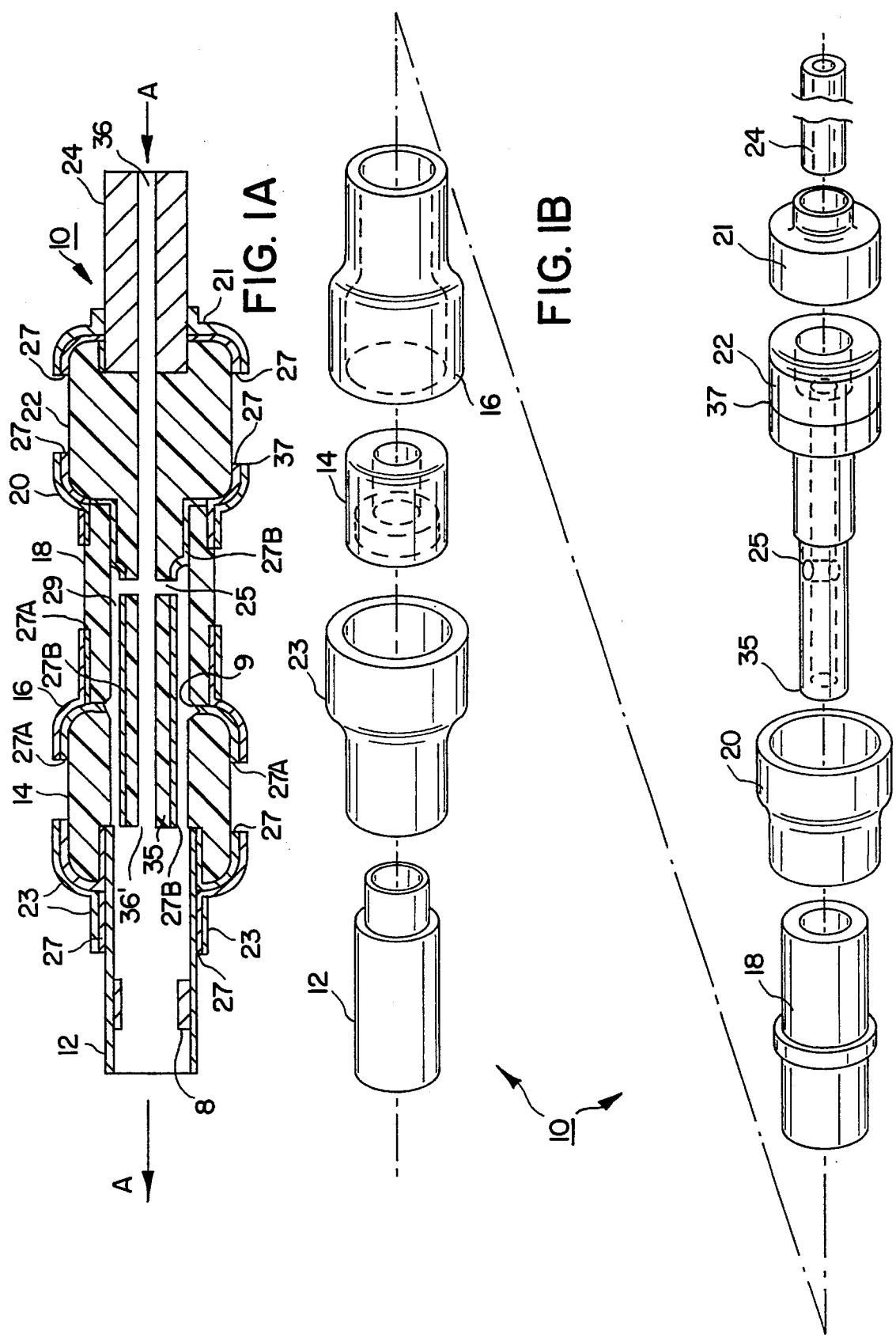

ELECTRON CAPTURE DETECTOR WITH GUARD ELECTRODE

FIELD OF THE INVENTION

This invention relates to electron capture detectors (ECD) and electron capture cells such as are used to analyze chromatography eluent gas and in particular to an electron capture detector cell with a third electrode to improve the linearity response.

RELATED PATENT

U.S. Pat. No. 4,117,332, assigned to the same assignee relates to ECDs and is incorporated herein by reference.

BACKGROUND OF THE INVENTION

An electron capture detector (ECD) is a sensor used to analyze gas (analyte). The ECD takes several forms. All the forms are characterized by a flow through cell containing pair of spaced apart insulated field electrodes in a chamber and a source of ionizing radiation. As the analyte flows through the chamber, an "extraction voltage" waveform is applied between the field electrodes. In the absence of gaseous compounds which can capture the electrons, a given cell current is produced. The resultant electron density within the chamber is affected by attachment of electrons to the analyte. Electron density is measured using an appropriate transducer, e.g. electrometer, to measure the current generated by the application of the extraction voltage waveform to the field electrode. Usually the ECD cell is connected into an oscillator circuit where the pulse frequency is proportional to the analyte concentration. At higher frequencies the insulation leakage loss of the ECD cell increase at a faster rate and the linearity of the device is diminished. At low frequency the cell insulation leakage established a minimum detection current level. Constant frequency devices which measure concentration as a function of current are also known.

To minimize the leakage currents between the ECD cell field electrodes, very high resistance insulators are usually employed to isolate the pulsed voltage waveform from the electrometer circuit, i.e. to insulate the anode from the cathode. Typical resistance values are of the order of one million megohms. Specific theoretical models such as the Maggs model or the Wells model ignore the possibility of leakage currents clue to low resistivity components or contamination of high resistivity components which, in practice, effectively decreases the observed resistance between the anode and cathode structures. ECD's have a large linear dynamic range but they typically do not perform as well as the theoretical models. In addition, the ECD linear range is very sensitive to contamination of the cell outer surface and it is temperature sensitive. The insulator supporting and separating the field electrodes exhibits a leakage current across or through the insulators and this leakage is consequently input into the measuring transducer (e.g. electrometer) resulting in a decrease of linearity of the response of the electron capture detector. This distortion results for pulsed waveforms in either constant frequency or constant current modes of operation.

SUMMARY OF THE INVENTION

It is an object of this invention to improve reliability of measurement of analyte concentration in a gaseous medium.

It is a further object to provide an electron capture detector which is characterized by improved linearity of measurement of electron charge density versus analyte concentration by eliminating leakage current across imperfect cell insulators due to constant or pulsed voltages or other voltage waveforms being applied.

It is still another object to eliminate loss of linearity of response of the electron capture detector due to extraneous influences such as is caused by contamination encountered in handling, packaging and shipping the device and differing temperature environments.

A feature of this invention is an electron capture detector cell having a third electrode, called a guard, positioned between the pulser and electrometer electrodes.

The addition of the guard electrode provides a path for diversion of the frequency dependent portion of the leakage current which flows between the ECD pulser and the electrometer. Tiffs is particularly important at very low concentration levels of analyte because the leakage current establishes the lowest ECD pulser frequency at the lowest measurable concentration of the analyte.

In an alternative arrangement, the guard electrode is connected between the pulser/electrometer lead and nominal system ground with the guard electrode being impressed with an identical voltage waveform but without the electrometer and associated feedback circuitry thereby reducing leakage current being introduced into the electrometer circuit.

Further, the guard electrode to the electron capture detector cell reduces the requirement for expensive high resistance insulators and decreases the care and cleanliness requirements for packaging, storage, and handling of the detector assembly. For operation in the constant current mode with low resistance (surface or bulk contaminated) insulators, the electron capture detector maintains linearity at high sample concentrations whereas the non-guarded electron capture detector simply ceases to respond to sample concentration (i.e. the pulser frequency will not increase beyond the operating point where the leakage current is sufficient to match the required reference current). An obvious advantage for the use of the invention is that the time between servicing of the detector can be increased making ownership and operational costs less expensive, and quantitation more reliable.

BRIEF DESCRIPTION OF THE FIGURES

FIG. 1A is a sectional view of an ECD cell with the guard electrode of this invention.

FIG. 1B is a perspective exploded view of FIG. 1A.

DESCRIPTION OF THE PREFERRED EMBODIMENT

Figure 2A:
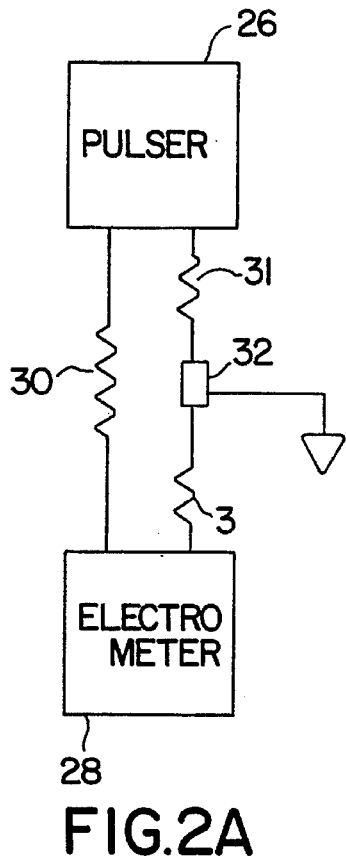
FIG. 2A is a schematic diagram of the ECD cell showing the grounded guard electrode.

Turning now to a discussion of the drawings, the following table lists features and identifying numerals shown in the drawings.

TABLE 1

IDENTIFYING FEATURES IN THE DRAWINGS

| | |
|---|---|
| 9 corner relief | 44 top insulator |
| 10 electron charge detector cell | 46 guard electrode |
| 11 field electrode | 48 bottom insulator |
| 12 cathode electrode | 50 electrometerelectrode |
| 13 guard electrode | 52 sample inlet or outlet |
| 14 insulator | 54 base mount |
| 15 field electrode | 56 base insulator |
| 16 guard electrode | 60 guard electrode |
| 17 resistor | 62 anode |
| 18 insulator | 66 sample outlet |
| 20 metal cap | 68 cathode |
| 21 base cap | 70 outer insulator |
| 22 insulator | 72 inner insulator |
| 23 cathode cap | 74 base insulator |
| 24 mounting tube | 78 sample inlet |
| 25 aperture | 82 electrodes |
| 26 pulser | 84 electrodes |
| 27 braze layer | 86 wall electrode |
| 28 electrometer | 88 guard electrode |
| 29 flow space | 92 sample inlet |
| 30 resistance | 94 base insulator |
| 31 insulator resistance | 96 anode #1 |
| 32 grounded guard electrode | 98 lower insulator #1 |
| 33 insulator resistance | 100 guard electrode #1 |
| 34 leakage resistor | 101 upper insulator #1 |
| 35 end of insulator 22 | 104 upper insulator #2 |
| 36 insulator bore | 106 guard electrode |
| 37 boundary of metalazed anode layer | 108 lower insulator #2 |
| 39 shoulder | 110 anode |
| 40 sample outlet | 112 exit insulator |
| 42 pulser electrode | 114 outlet tube |

FIG. 1A is a sectional view showing an electron capture detector 10 (ECD) cell with the guard electrode of this invention. FIG. 1B is an exploded perspective view of FIG. 1A. The cathode 12 is a metal cylinder 12 containing a radioactive foil source 8 (typically Ni-63).

A hermetic seal is formed between cathode cylinder 12 and the smaller diameter end of metal cap 23 via a braze layer 27. The other end of metal cap 23 is also hermetically sealed to an end of insulator cylinder 14. The end of insulator cylinder is metallized for adhesion to a braze layer 27. Braze layer 27 interfaces both metal cap 23 with insulator cylinder 14 as well as metal cap 23 and cathode cylinder 12. Braze layer 27 is shown throughout the structure to form hermetic seals between abutting parts.

The other end of insulator cylinder 14 is hermetically sealed to the larger diameter end of metal guard electrode 16. The other smaller end of metal guard electrode 16 is hermetically sealed to one end of field insulator cylinder 18. A layer of braze 27A, is shown between an end of insulator cylinder 14 and field insulator 18 and forms an electrically conducting interface between the metal guard electrode 16 and insulator 18 and insulator 14.

The anode comprises metal film 27B formed on an elongated portion of insulator 22 between end 35 and boundary 37 and metal cap 20. End 35 of insulator 22 is positioned through the bores of insulator 18 and into insulator 14 bore. The major body of insulator 22 is sealed to an end of insulator 18 by brazing (layer 27).

In the annular region 9 where the seal between insulators 14 and 18 border the sheath space 29, both the insulators 14 and 18 have their edges relieved so that during sealing the brazing can not bead across channel 29 and short the guard electrode 16 to the anode.

A mounting cylinder 24 is hermetically sealed to an end of insulator 22 by brazing 27 to metal cap 21.

Gas to be analyzed passes into bore 36 of the cylinder 24 (see arrow A) and the flow stream is divided at radial bore holes 25 in insulator 22, the major portion of the stream passing through the bore of insulator to exit at 36'. The part of the gas which passes through flow passage 29 also enters the bore of cylinder 12.

The secondary gas flow provided by bore 25 and annular flow passage 29 in parallel with flow passageway 36 and 36' generates a more laminar transition upon the exiting of the gas flow in the cathode region so as to make the profile of flow through the detector more laminar. Another advantage is that the flow through the annular flow passage 29 provides a "sweep" gas flow to keep the insulators well swept and provides a higher sheath gas flow along the walls of the cathode to minimize sample absorption on the radioactive foil.

Mounting of the ECD cell to a sample device (e.g. gc column effluent, sample gas stream, etc.) is by either a welding operation or by the use of ferrules, O-rings or other appropriate sealing technology.

This invention maintains the inertness of normal ECD design including the sweep flow but in addition this design provides greatly decreased leakage current and improves the linearity of the detector.

A block diagram of the equivalent circuit of the ECD with the guard rail of this invention is shown in FIG. 2A. A block diagram of the equivalent circuit of an ECD according to the prior art is shown in FIG. 3.

Figure 3:
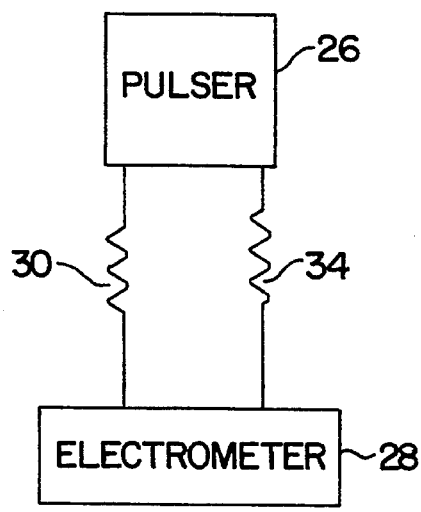
FIG. 3 is a schematic diagram of the ECD cell of the prior art.

Shown in both FIG. 2A and FIG. 3, is a pulser 26, an electrometer 28, and a resistance 30 representing the conductance of the gas phase cell. Conductance 34 in FIG. 3 represents the leakage of current across the insulators of the ECD cell. FIG. 2A shows the grounded guard electrode 32 of this invention between insulator resistance 31 between pulser and ground electrodes and insulator resistor 33 between ground and electrometer electrodes.

Typical parameters for operating the invention ECD with guard electrode design are listed in Table II.

TABLE II

| $t_p$ Pulser width 600 ns | | $R_{leak}$ 1 × 10$^{10}$ |
|---|---|---|
| $V_p$ Pulse amplitude −60 V | | $R_2$ 5 × 10$^9$ |
| $V_p$ Contact potential = 0.0 V | | $V_{electrometer}$ 1.0 mV |
| | Conventional Design | Guard Electrode |
| Frequency | Leakage Current (pA) | Leakage Current (pA) |
| 1.0 kHz | 3.6 | 0.200 |
| 10.0 kHz | 36.0 | 0.200 |
| 100.0 kHz | 360.0 | 0.200 |

Although I do not wish to be bound by theory, it is believed that the following analysis explains the dependence of operating characteristics of the invention on the guard electrode.

An appropriate expression which illustrates the response of the ECD for specific geometry, pulse voltage waveform, detector volume and foil activity operating in the constant frequency or constant current mode is given by the Magg's expression:

$$I\_electron = \{(kp*Q*volume*f)/(k_d + k_1*C)\}*\{(1-\exp(-(k_d+k_1*C)/f)\} \quad (1)$$

where I_electron=electron current measured by the current transducer kp=production rate of electrons, (ml/sec)
q=charge per electron, (coul/electron)
volume=volume of the detector, (ml)
f=pulse (waveform) frequency, (Hz)
$k_d$=recombination rate constant, (sec$^{-1}$)
$k_1$=attachment rate constant, and (ml/sec)
C=analyte concentration, (μ/ml)

Operation of the ECD in the constant current mode corresponds to changing the frequency of the pulser to maintain the constant current being measured by the current transducer at a constant value. In practice, this corresponds to comparing the measured current to a reference current (I_reference). The constant current circuitry then actively adjusts the pulser frequency to maintain equality between the reference and measured electron current so that $$I\_reference = I\_electron \quad (2)$$

However, since all insulators have real resistance, a leakage current always exists for classical (unguarded) designs which is given by:

$$I\_leakage = (V*t_p*f)/R\_insulator + V_{cp}/R\_insulator \quad (3)$$

where
I_leakage=leakage current across or through the insulator
V=pulser voltage
$t_p$=width of pulse (pulse duration).
f=pulser frequency
$V_{cp}$ contact potential across ECD cell
R_insulator=insulator resistance.

The addition of this term to the constant current model now requires that $$I\_reference = I\_electron + I\_leakage \quad (4)$$

Figure 4:
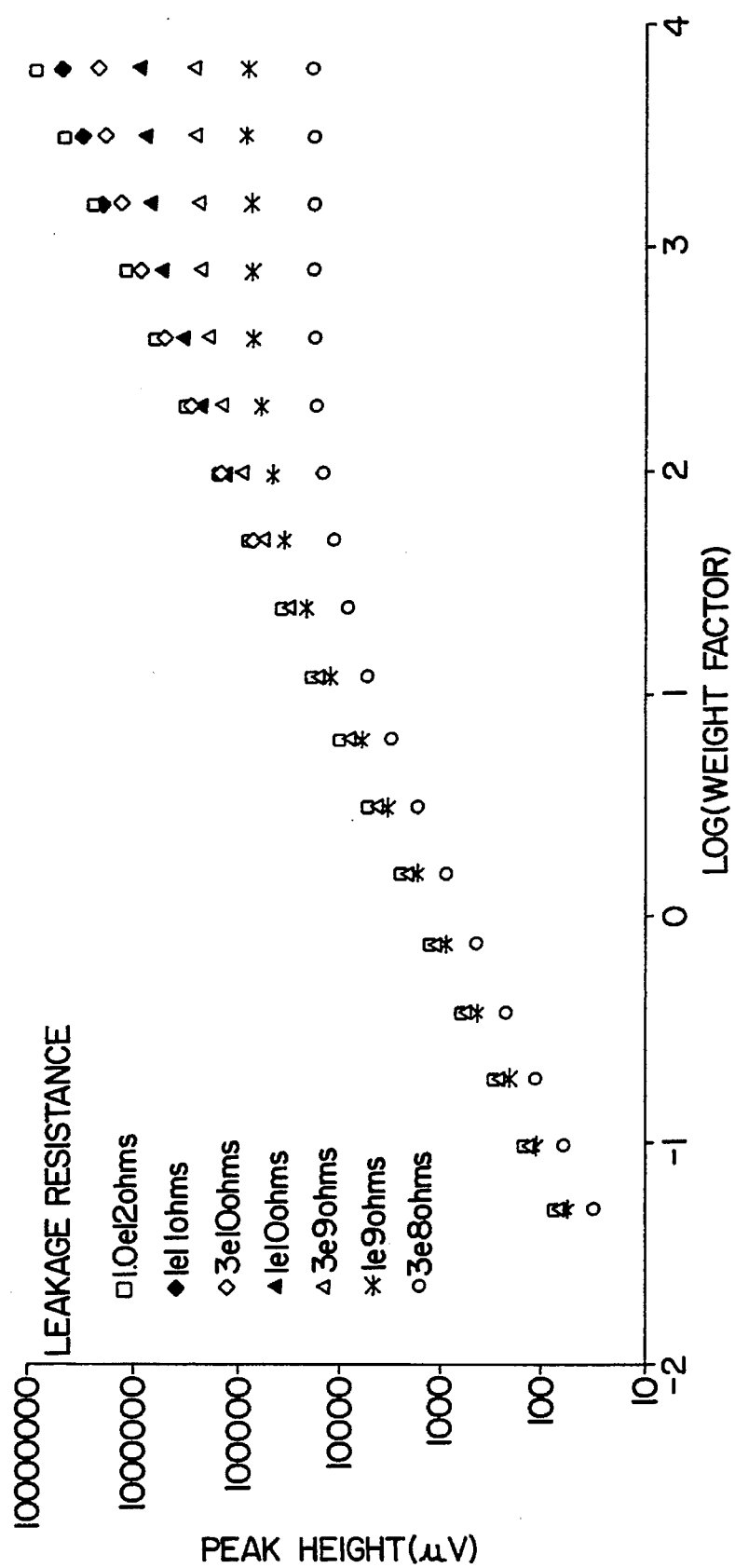
FIG. 4 is a plot of the Maggs model with leakage current.

FIG. 4 is a graph of the Magg's model with leakage current effects included. The graph plots the peak heights (proportional to frequency) required to maintain constant current between field electrodes as a function of concentration where log$_{10}$ (weight factor)=0 corresponds to 1.0×10$^{10}$ molecules/ml. Peak Height (uv)=(f−f$_o$) ×12800 uv/KHz where fo is the sample base frequency. In a ECD as analyte concentration increases, electrons are captured so that electron density decreases, and the pulser frequency increases to compensate for lower electron density and that I $_{13}$ leakage increases as I_electron decreases. For a standard ECD, if R_insulator is 10$^{10}$ ohms, V is 60 volts, $t_p$ is 600 nanoseconds, and Vcp is 0.0 volts from Table II, the leakage current at 1 kHz is 3.6 pA, at 10 kHz is 36 pA and at 100 kHz is 360 pA.

Comparing these leakage currents with nominal reference currents of 150 pA, 300 pA and 500 (pA) at the same frequencies, one would expect the response of the ECD without a guard electrode to be nonlinear, i.e., flatten, so that it is very difficult to accurately determine concentrations from this graph at high sample concentrations. This is confirmed by the Maggs model which includes the effects of leakage current as shown in FIG. 4 for the non-guarded ECD.

The addition of a guard electrode eliminates the dependence of the leakage current on frequency since the leakage current due to the pulser waveform is being diverted to ground. This is true even in the case of the pulser and electrometer being coupled into a single signal probe where the guard electrode is coupled to an equivalent pulser circuit without the electrometer and feedback control circuitry. In this case, leakage current is given as:

$$I\_leakage \text{ (guarded)} = V\_electrometer\_offset/R" \quad (5)$$

where:
v_electrometer_offset=electrometer input offset voltage, and
R"=resistance between guard electrode and anode (non pulsed electrode).

Even for a grossly incorrectly adjusted electrometer offset voltage of 1 mv, and a relatively low insulator resistance of 5.×10$^9$ ohms, which corresponds to a constant leakage current of 0.200 pA, the effect of this worst case is to decrease the reference current by only 0.200 pA. Since the reference currents have nominal values of 150 pA, 300 pA, 500 pA, this leakage current, being independent of frequency, does not decrease the linearity of the detector.

Figure 5:
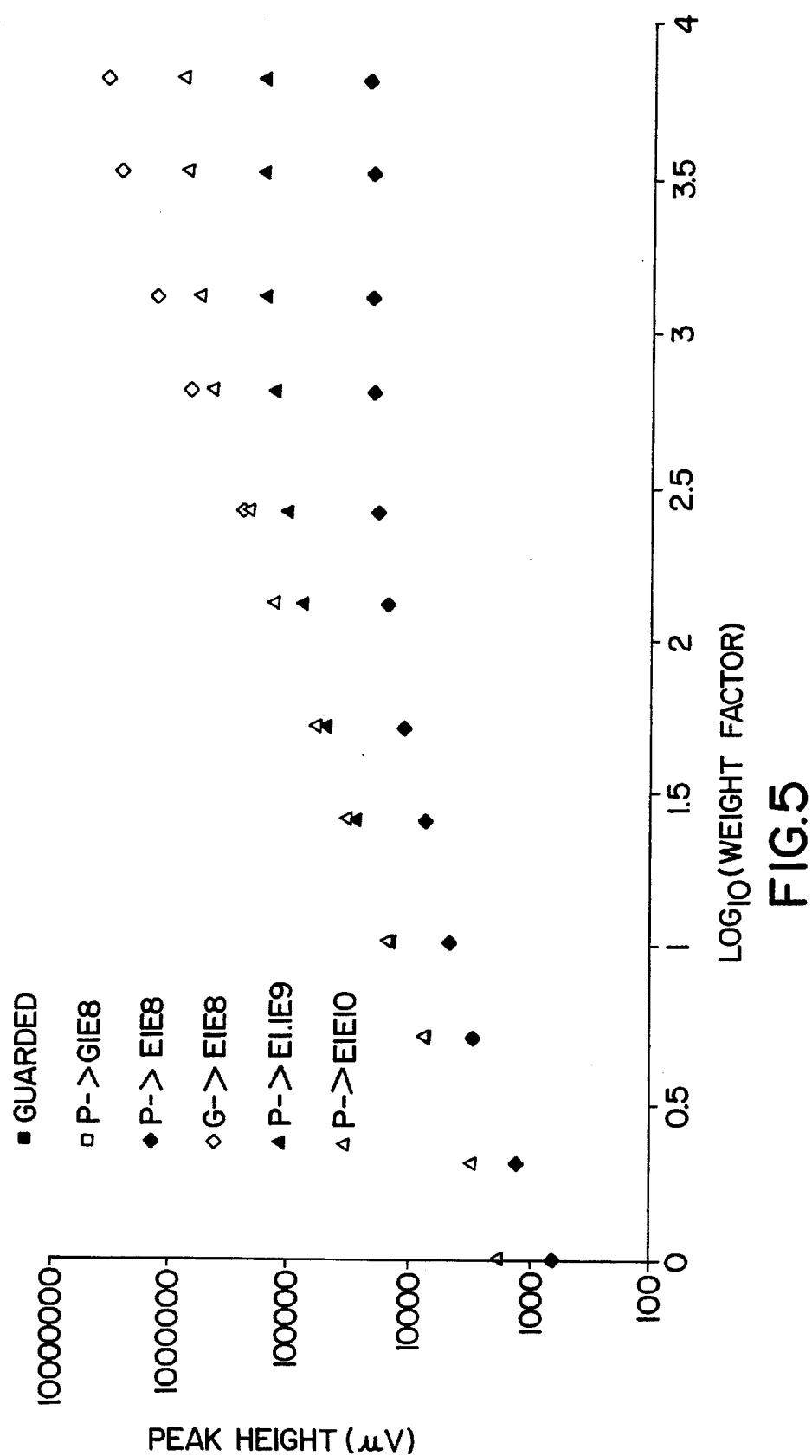
FIG. 5 is a graph showing experimental verification of Magg's model and the effect of leakage current on detector linearity.

With reference to FIG. 5, the line with the least curvature, i.e., the curve labelled "guard", corresponds to the guarded ECD of this invention.

Figure 13:
FIG. 13 is the customary connection of the ECD cell with guard electrode to be compared to the arrangements of FIGS. 11, 12, and 13.
Figure 12:
FIG. 12 is a schematic diagram of the ECD cell with guard rail and resistor between electrometer and guard terminals for experimental verification.
Figure 11:
FIG. 11 is a schematic diagram of the ECD cell with guard rail and resistor between pulser and electrometer terminals for experimental verification.
Figure 10:
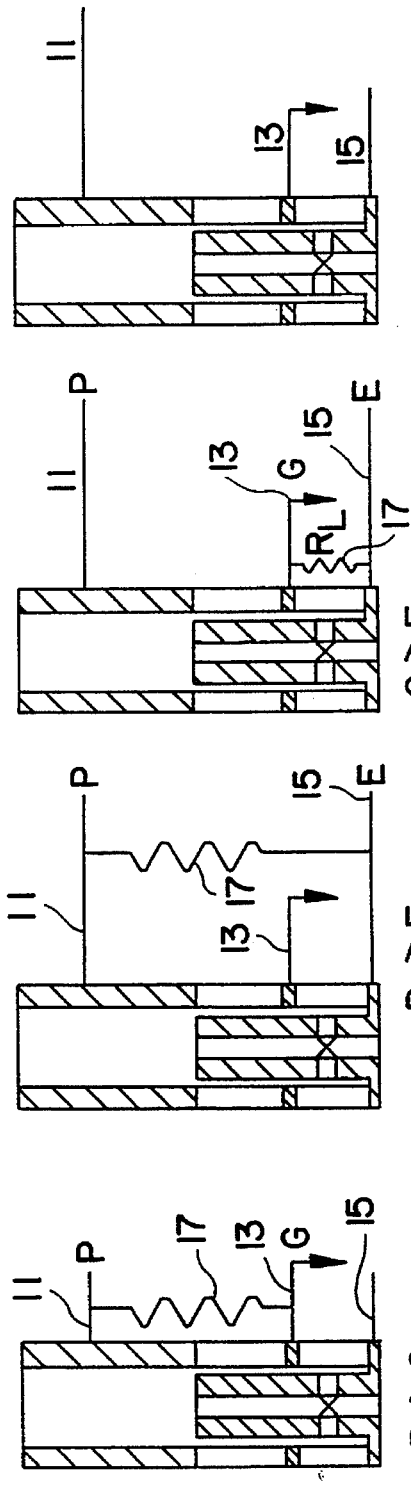

To verify the theory, experiments have been performed with the guarded ECD cells, FIGS. 10, 11, and 12 which show various experimental connections of the field electrode 11 connected to the pulser, the guard electrode 13, and the field electrode 15 connected to the electrometer. The various experiments involve attaching a resistor 17 between the pulser and guard electrodes ((P→G) (see FIG. 10), between the pulser and electrometer electrodes (P>E) (see FIG. 11) and between the guard and electrometer electrodes (G→E) (See FIG. 12.) The standard arrangement shown in FIG. 13 was used as baseline for comparison. Examination of FIG. 5, which shows response of the guarded ECD cell, clearly demonstrates the same effects as predicted by the modified Maggs model (i.e. for leakage current). All configurations which couple the pulser directly to the electrometer with a fixed resistor show deviation as predicted. Similarly, coupling the resistor through the guard electrode from either the pulser electrode or the electrometer electrode could not be distinguished from the standard guarded ECD response.

Other geometries of the ECD of this invention may be considered in addition to the displaced concentric cylinder construction discussed above. Also, if the current is being measured on the bias electrode, then the guard electrode should not be grounded, but should be connected to a pulser/bias circuit which must be matched in period, frequency, phase and d.c. offset voltage to eliminate the leakage current across or through the insulator.

Figure 2B:
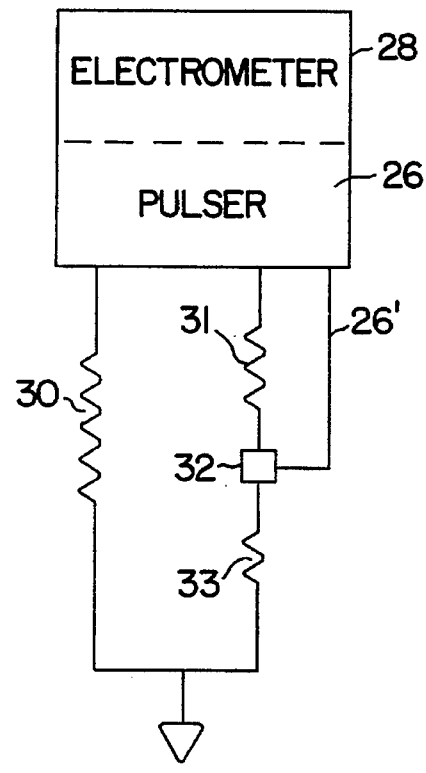
FIG. 2B is a schematic of the ECD cell showing a non-grounded guard electrode.
Figure 6A:
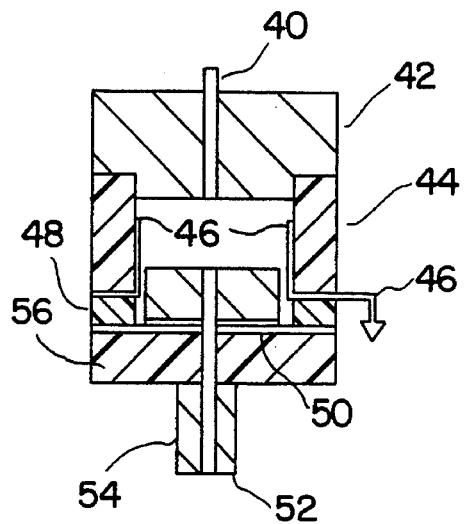
FIGS. 6A and 6B and 6C show three versions of a parallel plate construction of an ECD cell with guard electrode.
Figure 6B:
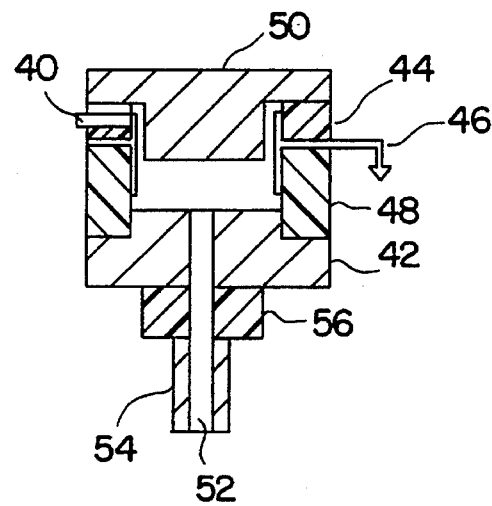
Figure 6C:
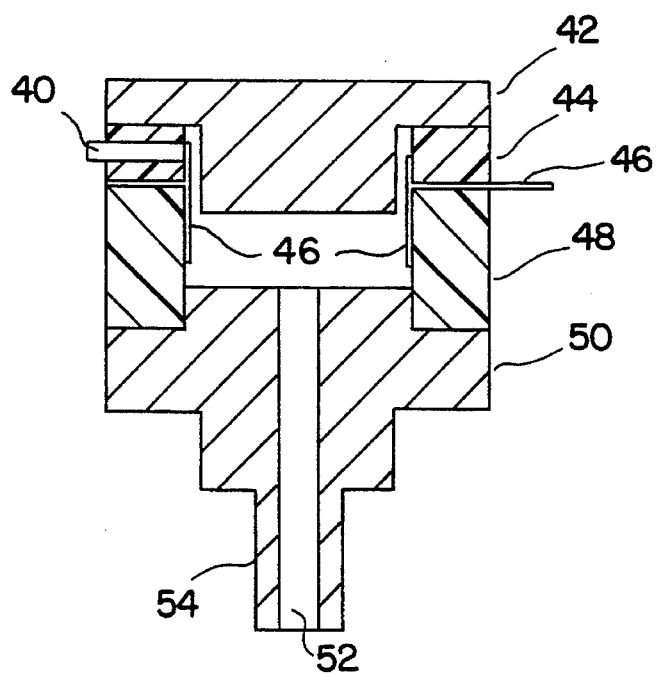

FIGS. 6A, and 6B show three versions of ECD cells employing a parallel plate configuration, each having a sample outlet or inlet, 40, pulser electrode 42, top insulator 44, grounded guard electrode 46, bottom insulator 48, electrometer (anode) electrode 50, sample inlet or outlet 52, base mount 54, base insulator 56. FIG. 6C is a version of parallel plate construction where the guard is to be connected through a pulser to ground. As shown in FIG. 2B, a pulser circuit 26 can be provided which includes a means of measuring the electron current. With this pulse source, it is possible to bias the guard electrode with a pulsing voltage 26' to cause the guard electrode voltage to track the pulser voltage.

Figure 7A:
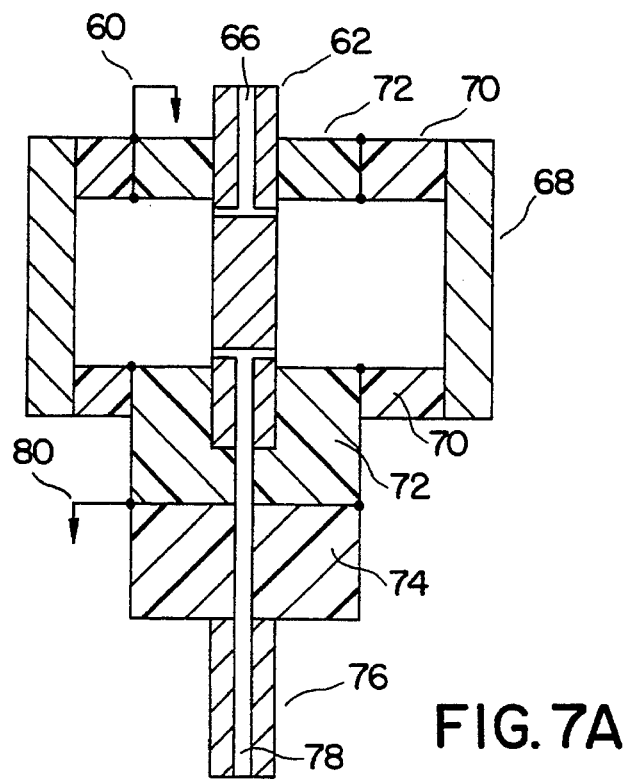
FIG. 7A and 7B show two versions of a concentric cylinder construction of the electrodes of the ECD cell of this invention.
Figure 7B:
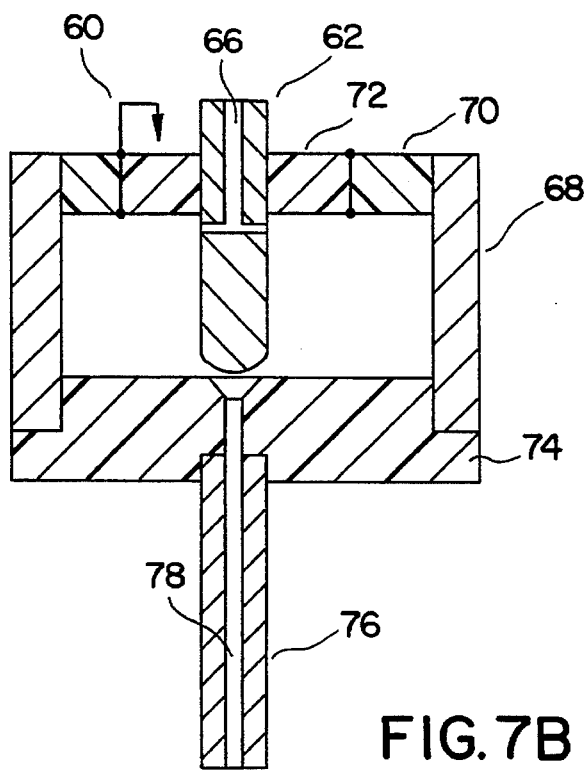

FIGS. 7A and 7B show two versions of an ECD cell employing a concentric cylinder configuration, each having a pair of guard electrodes 60, and 80 anode 62, sample outlet 66, cathode 68, outer insulator 70, inner insulator 72, base insulator 74, base mount 76, sample inlet 78.

Figure 8A:
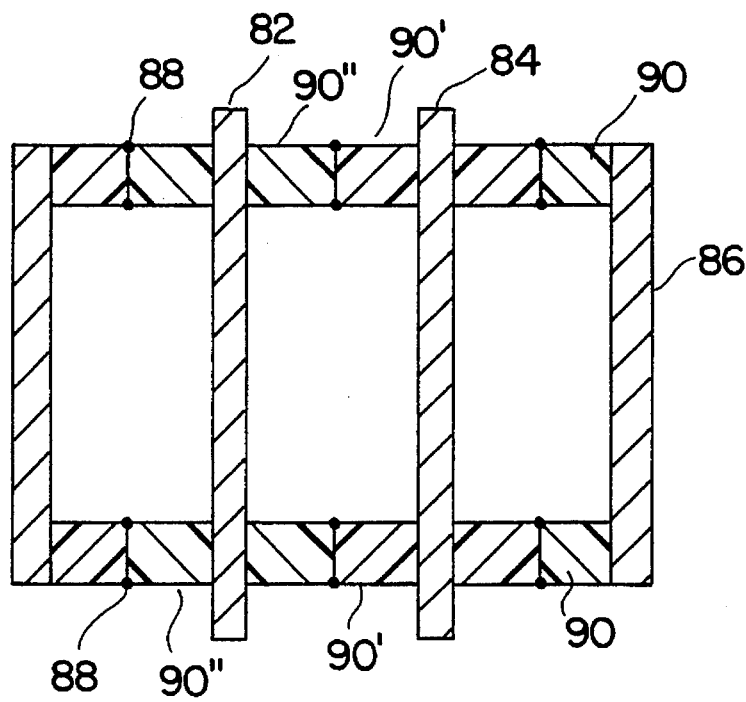
FIG. 8A is a sectional view of a multipole construction of an ECD cell with the guard electrode of this invention.
Figure 8B:
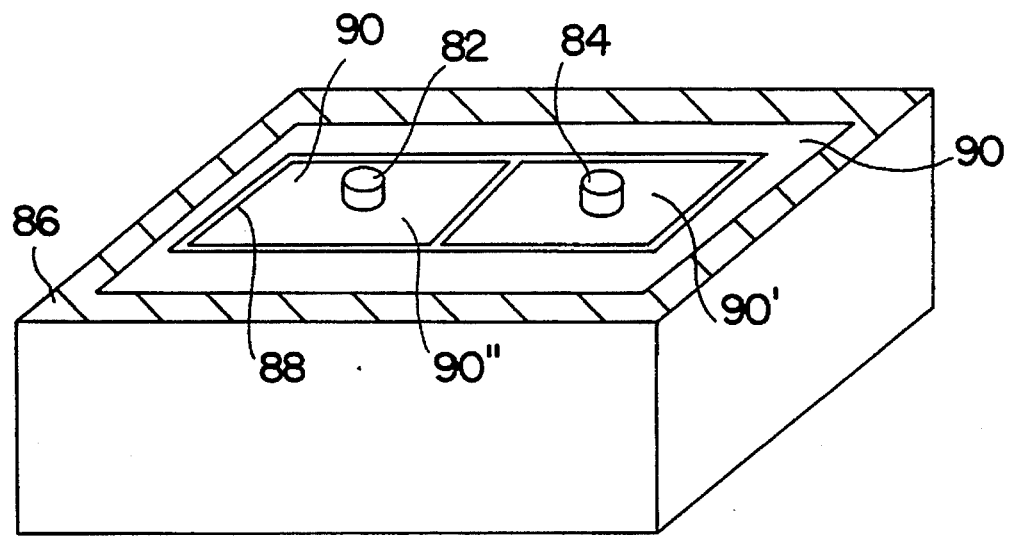
FIG. 8B is a perspective view of FIG. 9A.

FIG. 8A is a sectional view and FIG. 8B is a perspective view showing a multipoled ECD construction having electrodes 82 and 84, wall electrode 86, guard electrodes 88, and insulators 90.

Figure 9:
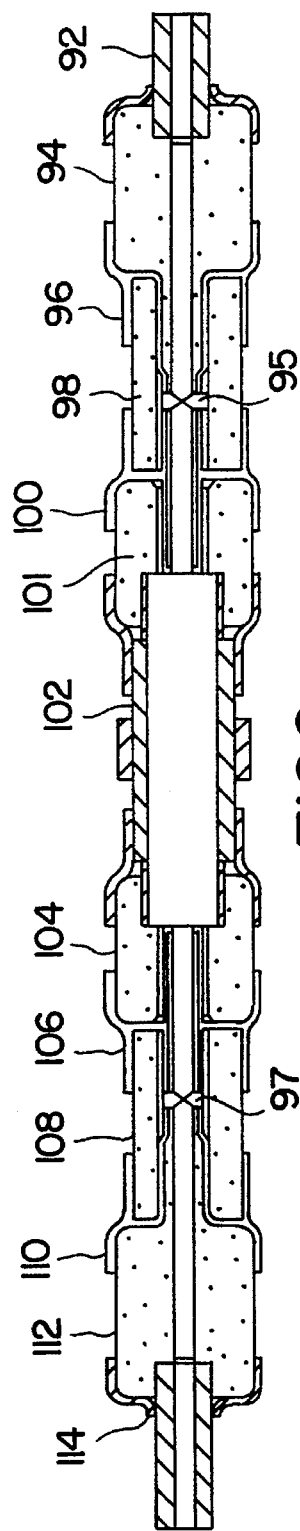
FIG. 9 is a sectional view of a multipole construction of the invention in greater detail than FIG. 10 is a schematic diagram of the ECD cell with guard rail and resistor between pulser and guard terminals for experimental verification.

FIG. 9 shows a cylindrical multipoled version in greater detail having a sample inlet 92, base insulator 94, anode #1,96, lower insulator #1,98, guard electrode #1 100, upper insulator #1, 101, cathode (or anode) 102, upper insulator #2, 104, guard electrode #2 106, lower insulator #2, 198, anode #2 [or cathode # 2] 110, exit insulator 112, outlet tube 114.

These ECD designs are not limited to use with constant current control but also can be applied in constant frequency mode as well as d.c. voltage modes. The waveform need not be singularly polarized but can also be a bipolar pulse.

The leakage current in the ECD cell with guard electrode of this invention has significantly improved the linearity of the detector. This permits quantitation and analysis by ECD electron attachment for species at higher concentrations levels. The guard also permits the detector to tolerate contamination which caused a reduction in resistance between the cathode and anode. Similarly, it permits construction of the detector with materials that would otherwise be unsuitable due to excessive leakage currents. Additionally, since the resistance of most all insulating materials decreases with increasing temperature, the guard electrode significantly reduces thermal effects with respect to leakage currents. However, the requirement that the electrometer input offset voltage be set to zero (i.e., balanced to signal ground) is still required. The addition of a guard electrode to the detector also serves to reduce the very strict cleanliness requirements for handling the prior art assembled detector. Effects of contamination of the exterior surface of a conventional ECD such as by manual manipulation or placing the detector on a contaminated surface has been solved by the guard electrode.

There are other alternative embodiments of my invention and accordingly, the scope of my invention should be determined by the following claims with this in view:

I claim:

1. An electron capture detector cell comprising:

a pair of field electrodes adapted for attachment to a source of voltage applied between said field electrodes;

insulation means for supporting said field electrodes such that said field electrodes are insulated and spaced from one another;

said supporting means defining an enclosed region containing said field electrodes and having at least one port to said region such as to admit a gas into said region;

means connected to said supporting means for reducing the leakage current which passes through said insulation means and which passes from one said field electrode to the other.

2. The apparatus of claim 1 wherein said means connected to said supporting means for reducing said leakage current includes a conductive guard electrode interposed between said field electrodes such that all possible current paths through said means for supporting from one said electrode to the other said electrode must intersect said conductive guard electrode.

3. The apparatus of claim 2 wherein either one of said field electrodes are connected to a source of pulses and the other of said field electrode is connected to an electrometer, and where said conductive guard electrode is connected to a terminal which is adapted for connection to an external source of voltage which is substantially equal in potential to the potential of said electrode connected to said electrometer.

4. An electron capture detector apparatus as in claim 3 wherein:

each said field electrode comprises an electrically conducting tube having a first open end and a second open end;

said means for supporting said conducting tubes comprises two insulator tubes, each said insulator tube having two open ends, one end of each said insulator tube secured to said second end of one of said conducting tubes respectively;

said other end of each said insulator tube joined to said conductive guard electrode;

said conducting tubes, insulator tubes and conductive guard electrode being connected in series with one another such as to permit gas to pass into said first end of one said conducting tube and exit from said first end of said other conducting tube.

5. An electron capture detector apparatus as in claim 4 wherein:

said conducting guard electrode is a tube having two ends, each end connected to one of said other ends of said insulator tubes respectively; and wherein said terminal is connected to said conducting guard tube.

6. An apparatus as in claim 2 wherein:

each said field electrode is a parallel electrode plate having a substantially flat surface;

said means for supporting said flat electrode plates is a pair of insulating tubes, each insulating tube having an end of said tube supportively abutting one of said flat surfaces of said electrode plates respectively such that said flat surfaces face one another;

said means for reducing leakage current being a flat guard plate having a pair of plane surfaces opposite one another with each plane surface abutting another end of one of said insulating tubes respectively;

said guard plate having a hole such that a region on one side of said guard plate communicates with a region on an opposite side of said guard plate;

one of said insulating tubes having a wall with an aperture through said wall permitting gases to pass through said aperture into said region between said electrode plates.

7. An apparatus as in claim 2 wherein:

each said field electrode is an electrode tube;

one said electrode tube having a diameter that is larger than a diameter of said other electrode tube;

said means for reducing said leakage current being a conductor guard having a diameter intermediate between said electrode tubes;

said electrode tubes and guard being supported concentric to one another by said supporting means, and said guard being interposed between said field electrodes to preclude any current path therebetween through said support means.

8. An electron capture detector apparatus comprising:
a plurality of electrodes adapted for attachment to a source of voltage applied between said electrodes;

means for electrically insulative supporting said electrodes such that said electrodes are insulated and spaced from one another;

said supporting means defining an enclosed region containing said field electrodes and having at least one port to said region such as to admit gas into said region;

means for supporting a radioactive ionization source within said region;

guard means connected to said supporting means for draining leakage current from said insulating means, said guard means adapted to be grounded in operation.

9. A method for analyzing composition of a gas which includes:

(a) passing said gas into a region containing a plurality of field electrodes wherein said field electrodes are supported in said region and spaced from one another by an array of insulators, said array of insulators provided with guard electrode means for reducing leakage current therebetween generated when an electrical potential is applied between said plurality of field electrodes and one said field electrode is an anode and the other is a cathode;

(b) applying an electrical potential to each of said field electrodes and simultaneously precluding leakage current by said guard electrode means between said field electrodes, and (c) measuring electron current flowing between said field electrodes as function of time to provide a spectrum of the electron affinity of said gas.

10. The method of claim 9 wherein said step of simultaneously precluding leakage current comprises connecting said guard electrode to a potential substantially the same as said anode potential.

11. An electron capture detector for analyzing gas comprising:

a first electrically conducting tube (12) having a first open end and a second open end;

a first insulator tube (14) having a third and a fourth open end, said third open end of said first insulator tube being hermetically sealed to said second open end of said first conducting tube;

a second insulator tube (18) having a fifth open end and a sixth open end;

a guard electrode (16), said guard electrode being a metal material; said guard electrode and said fifth open end and said fourth open end being hermetically brazed together to provide an electrically conducting path between all adjacent regions of said first insulator tube (14) and said second insulator tube (18);

a third insulator tube (22) having a first end section with a first outside diameter and a second end section with a second outside diameter wherein said second diameter is larger than said first diameter with a shoulder on said third insulator tube between said first and second sections, said first end section of said third insulator tube (22) being positioned inside said first and second insulator tubes;

said first end section of said third insulator tube having a wall with an opening (25), said second insulator tube (18) having an inside diameter such that a flow passage is formed between an outside surface of said first end section and an inside surface of said second insulator tube;

an elongated electrically conducting layer (27B) said elongated electrically conducting layer being on said outside surface of said first end section and on said shoulder (27) of said third insulator; and an anode electrode (20), said anode electrode and said shoulder and said sixth open end and said elongated electrically conductive layer being hermetically brazed together.

12. The apparatus of claim 2 wherein either one of said field electrodes is connected to ground and the other field electrodes is connected to a first pulsing voltage from a source, which source also includes pulse current measurement means, said apparatus further including means to connect said guard electrode to a second pulsing voltage which second pulse voltage is identical in timing with said first pulsing voltage, whereby said guard electrode and said current measurement electrode are maintained substantially equal in potential at all times.

13. The apparatus of claim 12 wherein:

each said field electrode comprises an electrically conducting tube having a first open end and a second open end;

said means for supporting said conducting tubes comprises two insulator tubes, each said insulator tube having two open ends, one end of each said insulator tube secured to said second end of one of said conducting tubes respectively;

said other end of each said insulator tube joined to said conductive guard electrode;

said conducting tubes, insulator tubes and conductive guard electrode being connected in series with one another such as to permit gas to pass into said first end of one said conducting tube and exit from said first end of said other conducting tube.

14. The apparatus of claim 13 wherein:

said conducting guard electrode is a tube having two ends, each end connected to one of said other ends of said insulator tubes respectively; and wherein said terminal is connected to said conducting guard tube.

15. In an electron capture detector (ECD) for detecting the presence and concentration of an analyte in a flowing carrier gas, said ECD including a variable frequency pulser circuit, an electrometer circuit and an electron capture detector cell, said electron capture detector cell having first and second separated field electrode mounted to an insulator, said variable frequency pulser circuit being connected to said first field electrode and said electrometer circuit between connected to said second field electrodes, said ECD having a feedback circuit to maintain the current in said ECD at a constant value irrespective of said analyte concentration, whereby the frequency of said variable pulse oscillator is directly proportional to the concentration of said analyte, THE IMPROVEMENT COMPRISING: a third electrode, said third electrode being physically located between said first and second electrodes and configured so that substantially all possible current paths through said insulator from one field electrode to the other field electrode must intersect said third electrode.

16. The ECD system of claim 15 wherein said third electrode is maintained at the same potential as said electrode connected to said electrometer.

* * * * *